Figure 1:
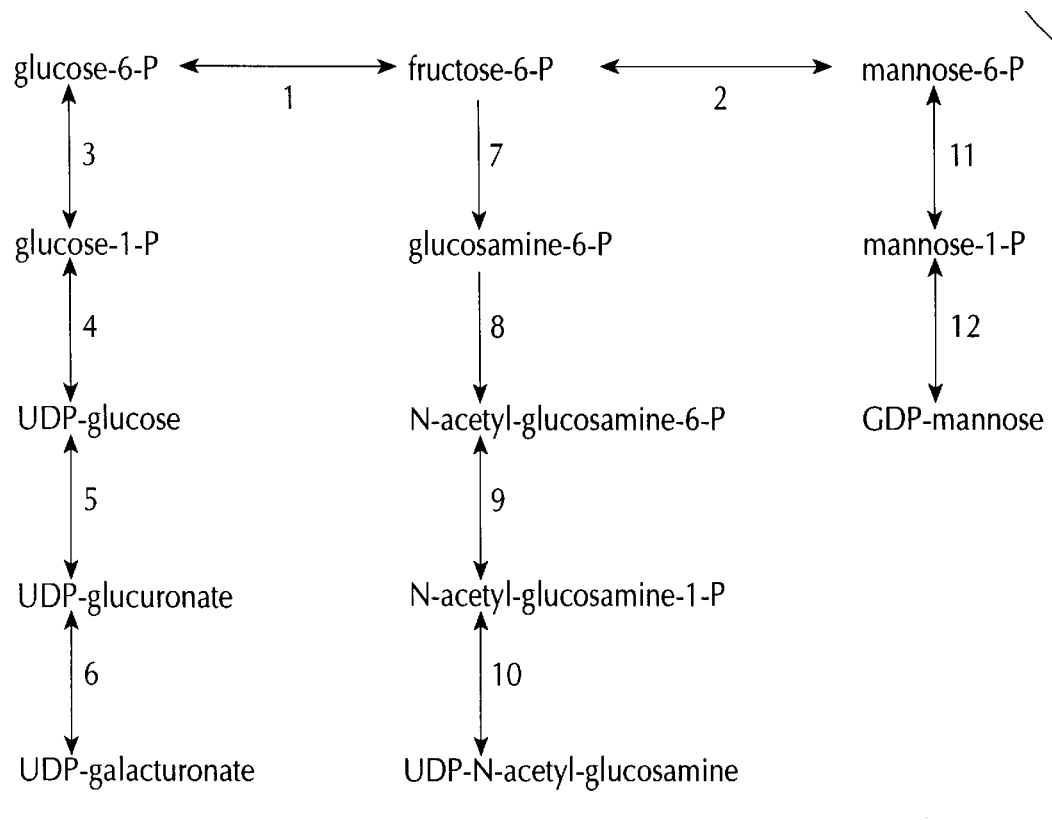
Figure 2A:
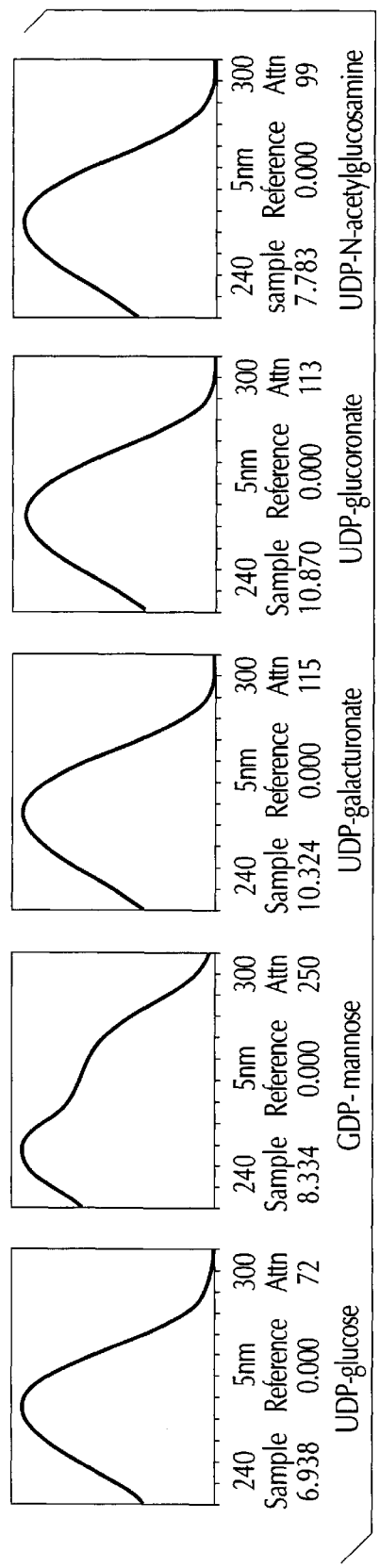
Figure 2B:
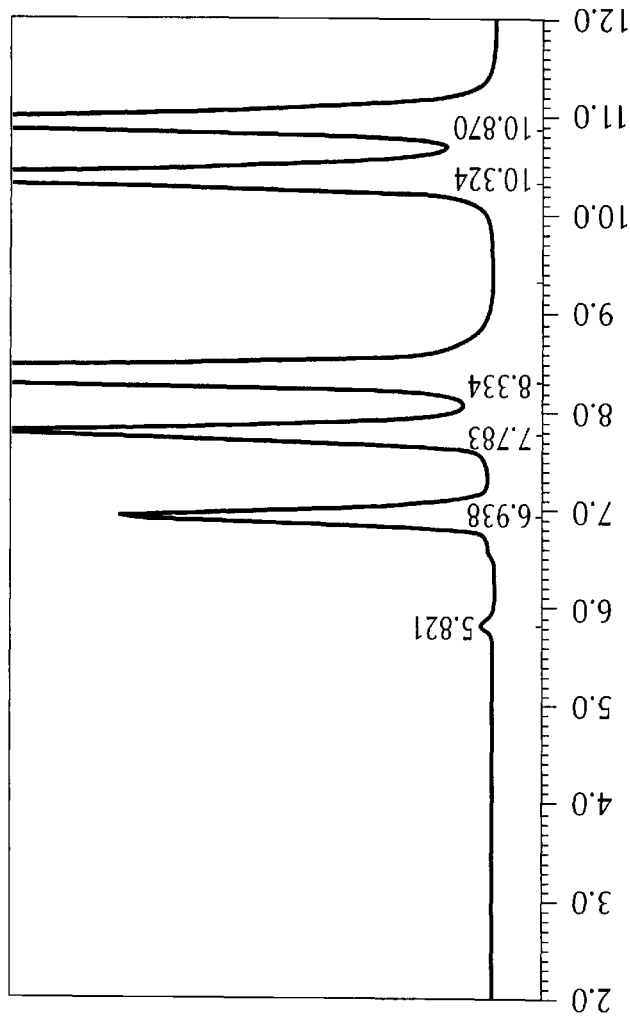
Figure 3A:
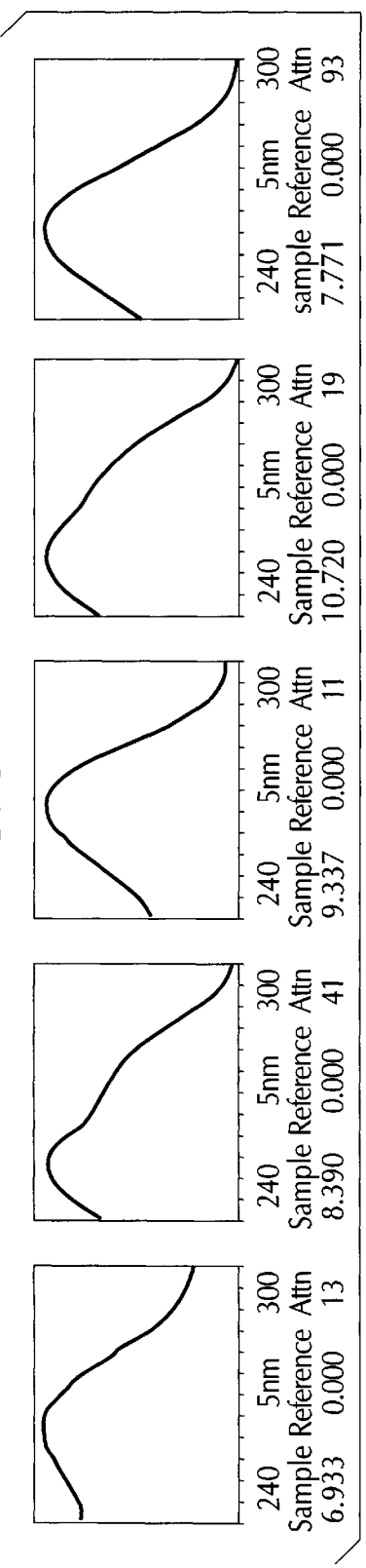
Figure 3B:
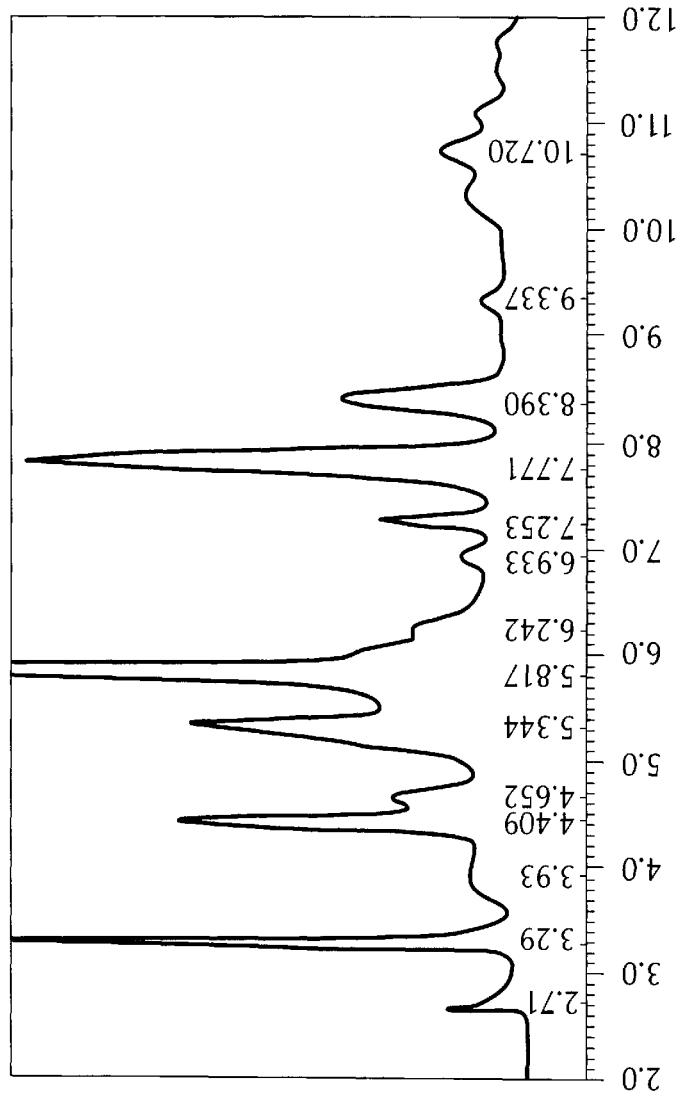
Figure 4A:
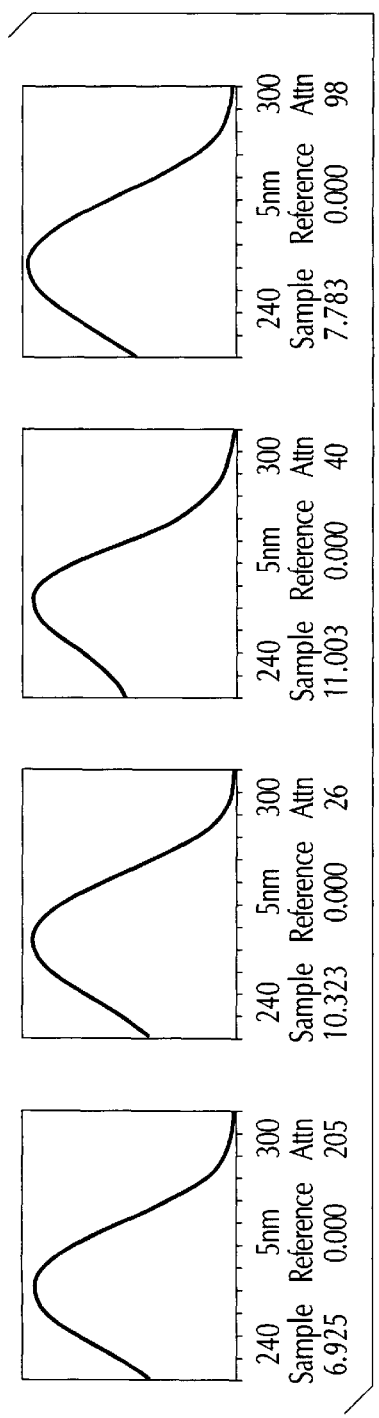
Figure 4B:
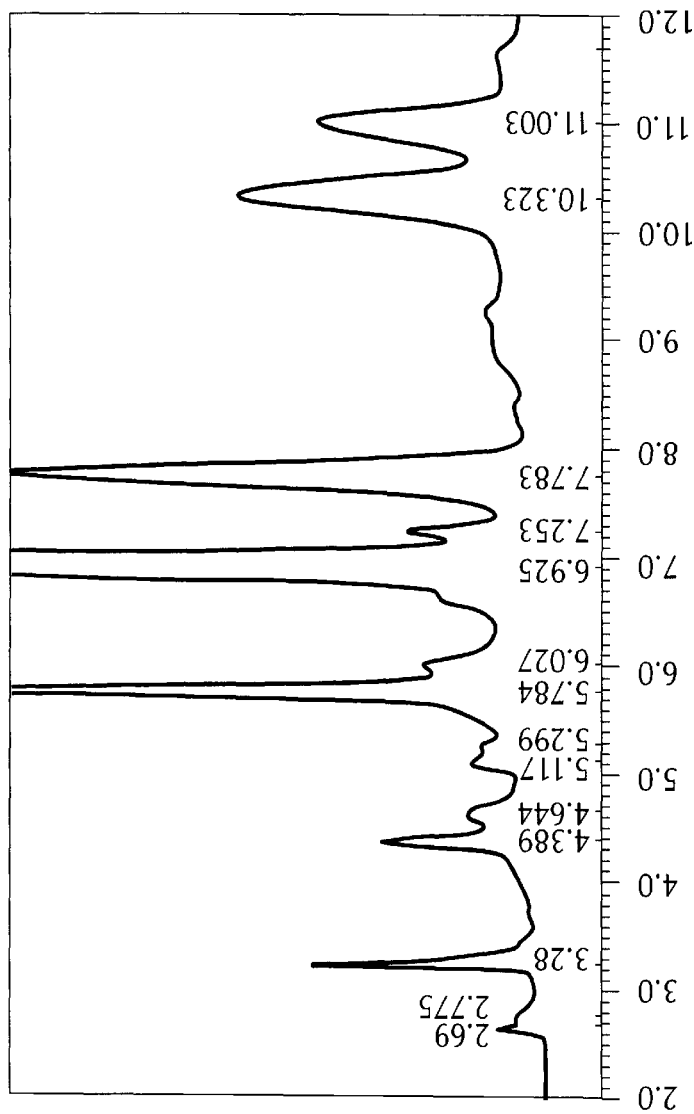
Figure 5A:
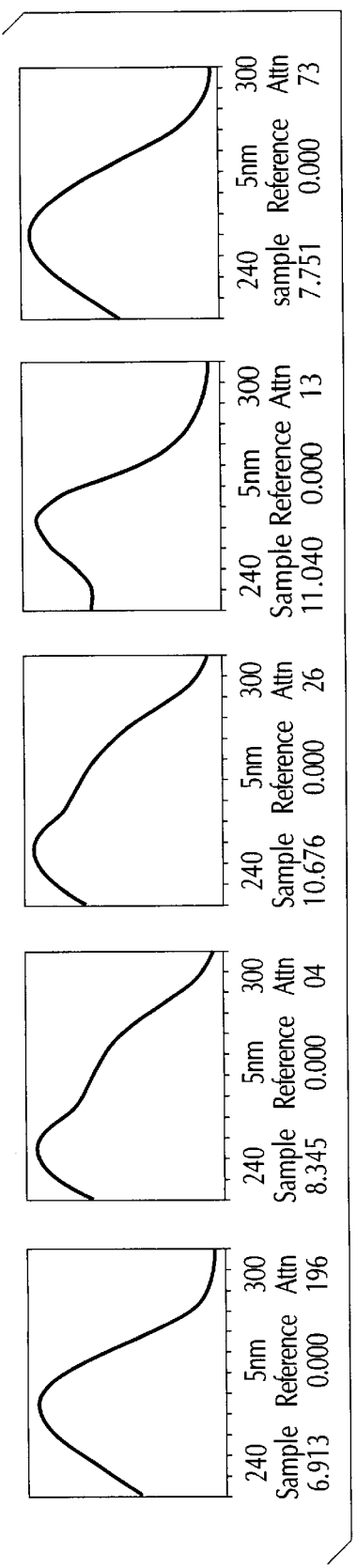
Figure 5B:
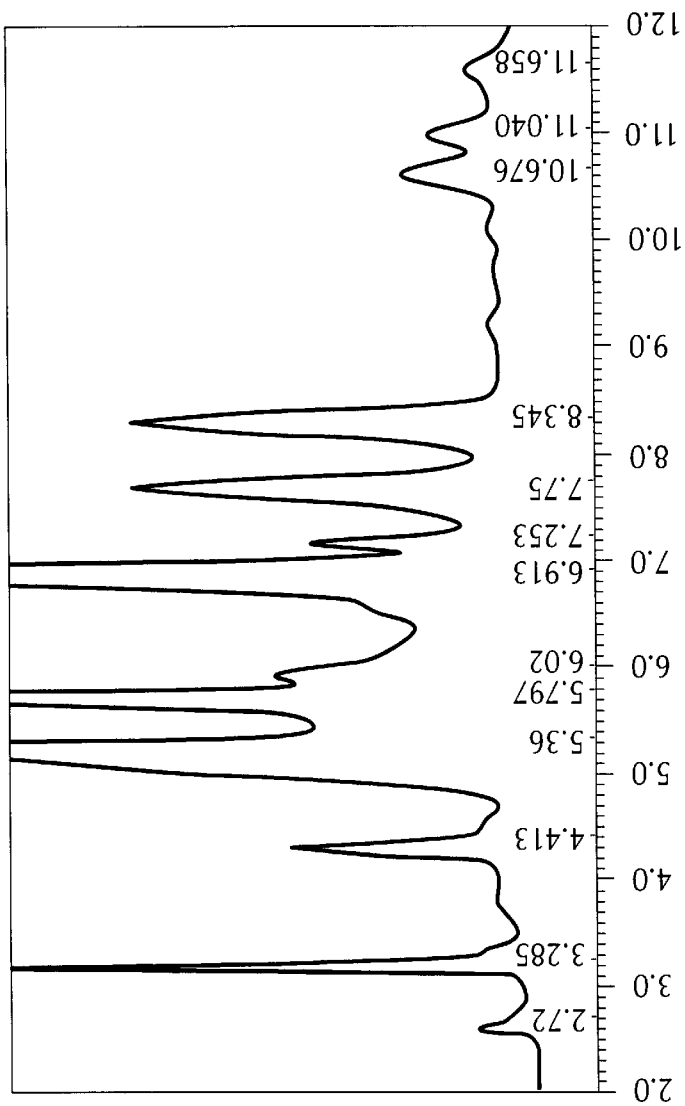
Figure 6A:
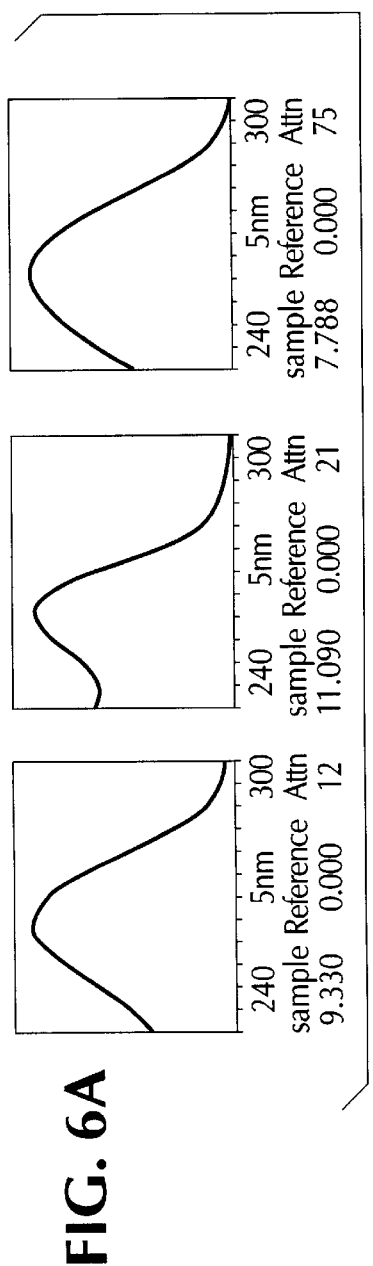
Figure 6B:
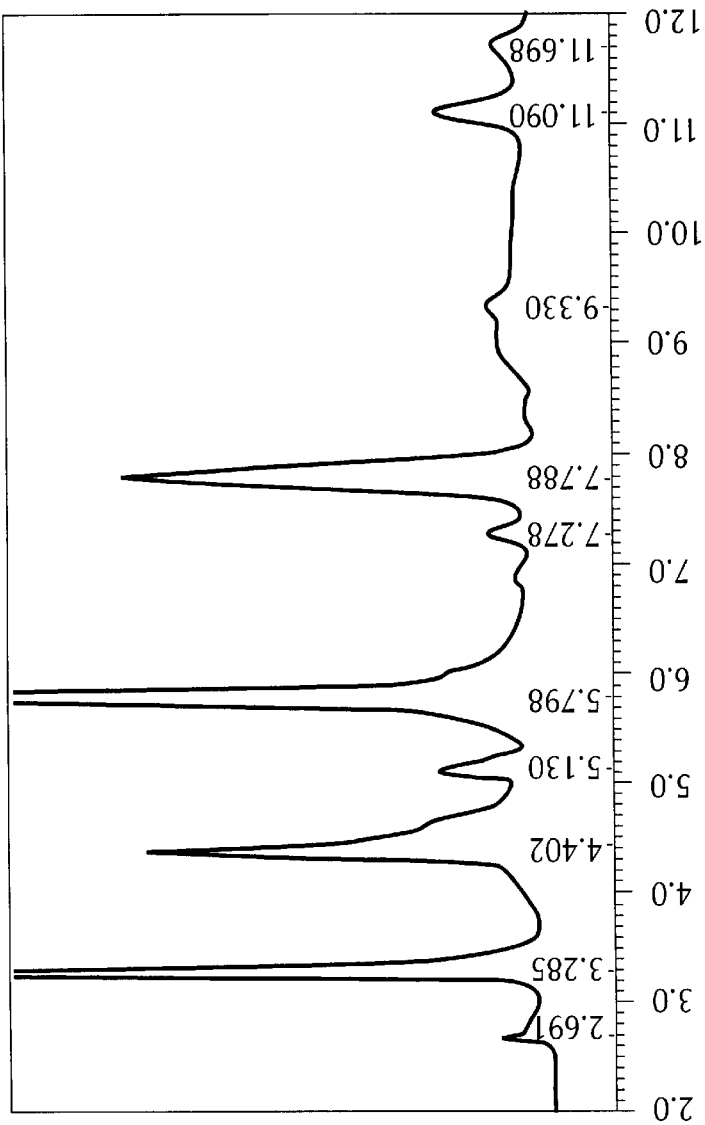

United States Patent [19]
Betlach et al.

[11] Patent Number: 5,824,472
[45] Date of Patent: Oct. 20, 1998

[54] PROCESS FOR THE SYNTHESIS OF SUGAR NUCLEOTIDES USING RECOMBINANT-DNA METHODS

[75] Inventors: Michael R. Betlach; Daniel H. Doherty; Rebecca W. Vanderslice, all of Boulder, Colo.

[73] Assignee: Monsanto Company, St. Louis, Mo.

[21] Appl. No.: 467,145

[22] Filed: Jun. 6, 1995

Related U.S. Application Data

[63] Continuation of Ser. No. 147,451, Nov. 5, 1993, abandoned, which is a continuation of Ser. No. 642,552, Jan. 18, 1991, abandoned, which is a continuation of Ser. No. 334,801, Apr. 3, 1989, abandoned, which is a continuation of Ser. No. 201,261, May 16, 1988, abandoned, which is a continuation of Ser. No. 29,091, Mar. 23, 1987, abandoned, which is a continuation-in-part of Ser. No. 843,349, Mar. 24, 1986, abandoned.

[51] Int. Cl.$^6$ .............................. C12Q 1/68; C12P 21/00; C12P 19/06; C12N 1/21
[52] U.S. Cl. ............................ 435/6; 435/69.1; 435/105; 435/252.3; 536/23.7
[58] Field of Search ................................. 435/69.1, 71.2, 435/91.1, 105, 183, 252.3, 172.3, 6, 14; 536/23.1, 23.7

[56] References Cited

U.S. PATENT DOCUMENTS

| | | | |
|---|---|---|---|
| 4,296,203 | 10/1981 | Wernau | 435/104 |
| 4,357,423 | 11/1982 | Cox et al. | 435/101 |
| 4,407,951 | 10/1983 | Weisrock et al. | 435/104 |
| 4,713,449 | 12/1987 | Vanderslice et al. | 536/123 |

FOREIGN PATENT DOCUMENTS

| | | |
|---|---|---|
| 66961 | 12/1982 | European Pat. Off. . |
| WO 87/05938 | 10/1987 | WIPO . |

OTHER PUBLICATIONS

U.S. application No. 07/333,285, Vanderslice et al., filed Apr. 5, 1989.
U.S. application No. 07/029,090, Doherty et al., filed Mar. 23, 1987.
U.S. application No. 07/384,621, Doherty et al., filed Jul. 25, 1989.
U.S. application No. 07/333,868, Capage et al., filed Apr. 3, 1989.
Buchanan et al., Journal of Bacteriology, 115:1011–1020 (1973).
E.S. Creeqer et al., J. Biol. Chem., 254:811–815 (1979).
R.P. Silver et al., Nature, 289:696–698 (1981).
S.K. Kadam et al., J. Bacteriol., 161:277–284 (1985).

(List continued on next page.)

*Primary Examiner*—Nancy Degen
*Assistant Examiner*—William Sandals
*Attorney, Agent, or Firm*—Fitzpatrick, Cella, Harper & Scinto

[57] ABSTRACT

A recombinant-DNA mediated method for the synthesis of sugar nucleotides is disclosed. This method utilizes portable DNA sequences capable of directing the microbial synthesis of various enzymes that catalyze the synthesis of sugar nucleotides, including UDP-glucose, UDP-glucuronic acid and GDP-mannose. The sugar moieties of these sugar nucleotides may subsequently be incorporated into industrially-useful polysaccharides such as xanthan gum. It has been found that vectors containing the portable DNA sequences described herein are capable both of causing sugar nucleotide production in microorganisms previously incapable of such synthesis and of causing increased sugar nucleotide production in organisms capable of synthesizing small quantities of these compounds. In particular, plasmids pAS7, pAS9 and pTS13 are disclosed. These plasmids are capable of directing sugar nucleotide synthesis in various hosts, including Xanthomonas sp. such as *X. campestris* and other organisms such as *E. coli* and various Pseudomonas sp.

30 Claims, 12 Drawing Sheets

OTHER PUBLICATIONS

A. Darzins et al., J. Bacteriol., 159:9–18 (1984).
A. Darzins et al., J. Bacteriol., 161:249–257 (1985).
J.B. Goldberg et al., J. Bacteriol., 158:1115–1121 (1984).
S. Gottesman et al., J. Bacteriol., 162:1111–1119 (1985).
R.C. Goldman et al., J. Bacteriol., 163:256–261 (1985).
Darzins et al., J. Bacteriol., 164:516–524 (1985).
Okita et al., J. Biol. Chem., 256:6944–6952 (1981).
Joyce et al., J. Biol. Chem., 257:1958–1964 (1982).
Gay et al., J. Biol., 153:1424–1431 (1983).
Ditta et al., Plasmid, 13:149–153 (1985).
Fishel et al., Develop. Biol., 110(2):369–381 (1985).
Couto et al., J. Biol. Chem., 259:378–382 (1984).
Creeger et al., J. Biol. Chem., 254:804–810 (1979).
Adhya et al., J. Bacteriol., vol. 108(2):621–626 (1971).
Kuriki et al., J. Biochem., vol. 58(3);308–311 (1965).
Daniels et al., EMBO J, vol. 3(13):3323–3328 (1984).
V. Deretic et al., Journal of Bacteriology, vol. 169, No. 1, pp. 351–358 (1987).
Souw et al., Appl. Environ. Microbiol., vol. 37, pp. 1186–1192.
European Search Report dated Mar. 28, 1997.

FIG. 7

The UDP-glucose, UDP-glucoronic acid, and UDP-galacturonic acid mutation is located elsewhere on the Xanthomonas chromosome, but not within the gum gene cluster

```
         ▽
     ┌───x649────┐
─────┤           ├──── Xanthomonas chromosome
      6.5 kb
UDP- glucocose ⊖
UDP- glucuronic acid ⊖
UDP- galacturonic acid ⊖
```

Wild type X. campestris("Xc")
PstI fragment with
homology to x649

— λ₁₀₅₉ ──┤── 6.5 kb ──┤── λ₁₀₅₉ ──

6.5 kb PstI fragment is subcloned into pBR322 pTf 6.5 (plasmid: 6.5kb Xc DNA in pBR322)

pTf 6.5 is cloned into RSF1010 plasmid pTS 13 (6.5kb Xc DNA and pBR322 in RSF1010)

FIG. 9

GDP-Mannose defective mutants are clustered on the Xanthomonas chromosome, but not within the region of DNA containing gum genes.

```
      ▽
     X652*
     X657      ▽
     X712    X711
   ──┼────────┼────┼──── Xanthomonas chromosome
     1.0 kb  0.95 kb
        GDP-
      MANNOSE ⊖
```

\* Mutant X652 is also defective in the biosynthesis of UPD-glucose and related compounds.

Large fragments of wt Xanthomonas chromosome are packaged into λ-1059.

```
                 wild type Xc Bam HI fragment
                       with homologgy
                          to X652
── λ₁₀₅₉ ──┼─────────────────────────┼── λ₁₀₅₉ ──
                       9 kb
```

9kb Bam HI fragment is cloned in expression vector pMW79 plasmid pAS7 pMW79

PROCESS FOR THE SYNTHESIS OF SUGAR NUCLEOTIDES USING RECOMBINANT-DNA METHODS

This is a continuation of application Ser. No. 08/147.451, filed Nov. 5, 1993 now abandoned which is a continuation of application Ser. No. 07/642,552 filed Jan. 18, 1991 now abandoned; which is a continuation of application Ser. No. 07/334,801, filed Apr. 3, 1989 now abandoned; which is a continuation of application Ser. No. 07/201,261, filed May 16, 1988 now abandoned; which is a continuation of application Ser. No. 07/029,091, filed Mar. 23, 1987 now abandoned; which is a continuation-in-part of application Ser. No. 06/843,349 filed Mar. 24, 1986, now abandoned.

BACKGROUND OF THE INVENTION

The present invention relates to recombinant-DNA methods for the production of various sugar nucleotides, which sugar moieties may be subsequently incorporated, also using recombinant-DNA methods, into microbially-produced polysaccharides.

It has long been known that certain microorganisms are capable of producing various industrially-useful polysaccharides. As a precedent to polysaccharide biosynthesis, these microorganisms must have a source of sugar nucleotides to construct the poly-saccharides. In the case of *Xanthomonas campestris,* a microorganism capable of producing xanthan gum, it has been found that the sugar nucleotides UDP-glucose, GDP-mannose and UDP-glucuronic acid are all direct precursors in the biosynthetic pathway. Thus, in elucidating the pathway for xanthan biosynthesis, the present inventors have discovered the DNA sequences responsible for sugar nucleotide synthesis in *X. campestris* and have developed recombinant-DNA methods for the production of these sugar nucleotides in both Xanthomonas sp. and alternate hosts.

The development of these methods for increasing sugar nucleotide production in Xanthomonas sp. naturally capable of producing xanthan gum should enable increased production of this polysaccharide by these organisms. It has been found that, although there are detectable levels of the sugar nucleotide precursors in these organisms, these levels are low. It has also been noted that in Xanthomonas organisms, wherein there is a mutation in the portion of the biosynthetic pathway responsible for polysaccharide assembly, the intracellular quantities of these sugar nucleotide precursors increase two- to seven-fold. Thus, it is believed that a rate-limiting step in natural xanthan production might be the sugar nucleotide precursor concentration and that the intracellular sugar nucleotide concentration can be increased by introduction of additional DNA sequences capable of directing sugar nucleotide production.

It has also been found that certain microorganisms which may be deemed desirable as alternate hosts for use in recombinant-DNA methods for the production of xanthan gum, generally either do not produce the required sugar nucleotide precursors or do not produce them in sufficient quantities to allow for xanthan production. Such recombinant-DNA methods and examples of the alternate hosts currently contemplated are set forth in U.S. Pat. No. 5,559,015 of Michael A. Capage et al. entitled "Recombinant DNA-Mediated Production of Xanthan Gum." In these methods, it is therefore necessary to induce the alternate host to produce the required sugar nucleotide precursors in addition to expressing the xanthan biosynthetic genes. The instant invention in part provides such a method.

Moreover, the present method may be used to induce sugar nucleotide production where the sugars are intended to be incorporated into polysaccharides other than xanthan. For example, various other gums have been identified which are altered versions of xanthan which require some or all of the instant sugar nucleotides as biosynthetic precursors. These gums include the polytrimer gum described in co-pending U.S. Pat. application Ser. No. 762,878 now abandoned of Vanderslice et al. entitled "A Polysaccharide Polymer Made by Xanthomonas" filed Aug. 6, 1985.

In addition, it is contemplated that the recombinant-DNA methods for producing sugar nucleotides disclosed herein may be mused for the production of certain polysaccharides of interest in part as medicinal or pharmaceutical preparations. For example, the polysaccharide colonic acid, produced by *E. coli,* is contemplated as a potential synthetic antigen useful for vaccination purposes. It is believed that production of colonic acid would be initiated or enhanced by the increased microbial production of the precursor sugar nucleotides.

Introduction of the DNA sequences into other microbial species may also enhance production of sugar nucleotides directed by such sequences since normal regulatory mechanisms controlling expression and activity may not be effective with foreign DNA or enzymes. In addition, many antibiotics, for instance the general class of macrolide antibiotics produced by Streptomyces species, have sugar moieties derived from sugar nucleotide precursors. The recombinant DNA methods for producing sugar nucleotides could be applied to such organisms increasing the availability of precursors essential for biosynthesis of the antibiotics.

SUMMARY OF INVENTION

One object of the present invention is to provide a method for the recombinant-DNA mediated production of sugar nucleotides. It is contemplated that these sugar nucleotides may be used in the in vivo synthesis of various polysaccharides, particularly in the synthesis of xanthan and novel polysaccharides structurally related to xanthan described more fully in the U.S. Pat. application Ser. No. 844,435 of Doherty et al. entitled "Family of Xanthan-Based Polysaccharide Polymers Including Non-Acetylated and/or Non-Pyruvylated Gum and Acetylated or Non-Acetylated Polytetramer Gum" filed Mar. 26, 1986 now abandoned.

To facilitate the recombinant-DNA mediated synthesis of these sugar nucleotides, it is a further object of the present invention to provide vectors containing these portable sequences. These vectors are capable of being used in the recombinant systems to produce quantities of the sugar nucleotides sufficient to create microbially-produced polysaccharides.

Additional objects and advantages of the invention will be set forth in part in the description or may be learned from practice of the invention. The objects and advantages may be realized and attained by means of the instrumentalities and combinations particularly pointed out in the appended claims.

To achieve the objects and in accordance with the purposes of the present invention, methods for the production of sugar nucleotides are set forth. The sugar moieties of such sugar nucleotides may be incorporated, using the methods and vectors set forth in U.S. Pat. No. 5,559,015 of Michael A. Capage et al. entitled "Recombinant DNA-Mediated Production of Xanthan Gum," into polysaccharides such as xanthan.

The portable DNA sequences may be either synthetic sequences or restriction fragments ("natural" DNA sequences). In a preferred embodiment, portable DNA sequences are isolated from an *X. campestris* library and are capable, when transferred into an alternative host, of directing the production of at least one sugar nucleotide.

Additionally, to achieve the objects and in accordance with the purposes of the present invention, a recombinant-DNA mediated method is disclosed which results in microbial manufacture of sugar nucleotides which can be used to produce xanthan gum and other polysaccharides using the portable DNA sequences referred to above. This recombinant DNA method comprises:

a) preparation of at least one portable DNA sequence capable of directing an alternate host microorganism to produce at least one sugar nucleotide;
b) cloning the portable DNA sequence into a vector capable of being transferred into and replicating in a host microorganism, such vector containing elements for expression of the portable DNA sequence encoding the biosynthetic enzymes;
c) transferring the vector containing the portable DNA sequence into a host microorganism capable of producing the biosynthetic enzymes for sugar nucleotide synthesis under the direction of the portable DNA sequence;
d) culturing the host microorganism under conditions appropriate for maintenance of the vector and synthesis of the sugar nucleotides; and optionally
e) harvesting the sugar nucleotides.

To further accomplish the objects and in further accordance with the purposes of the present invention, a series of plasmids are provided, each of which contains at least one of the portable DNA sequences discussed above. In particular, plasmids pAS7, pAS9, and pTS13 are disclosed. In addition, a mutant strain of *X. campestris,* strain X872, is provided which is deficient in phosphoglucomutase. *Xanthomonas campestris* strain X872 has been deposited on Mar. 21, 1986 in the American Type Culture Collection (ATCC), Rockville, Md., under Accession No. 53471. *E. coli* LE392 (pAS9); bearing plasmid pAS9, *E. coli* LE392(pAS7), bearing plasmid pAS7; and *E. coli* LE392 (pTS13), bearing plasmid pTS13, have been deposited on Mar. 21, 1986 in the ATCC under Accession Nos. 67050, 67048 and 67047, respectively.

It is to be understood that both the foregoing general description and the following detailed description are exemplary and explanatory only and are not restrictive of the invention, as claimed. The accompanying drawings, which are incorporated in and constitute a part of this specification, illustrate various embodiments of the invention and, together with the description, serve to explain the principles of the invention.

BRIEF DESCRIPTION OF THE DRAWINGS

FIG. 1 is a depiction of the biosynthetic pathways for the synthesis of UDP-glucose, UDP-glucuronate and GDP-mannose.

FIG. 2 depicts the separation of UDP-glucose, GDP-mannose, UDP-galacturonic acid, and UDP-glucuronic acid in a standard mixture by high performance liquid chromatography. UDP-N-acetylglucosamine served as an internal standard. Ultraviolet spectra from 240 to 300 nm are shown for each compound.

FIG. 3 depicts a chromatogram of a cell extract from strain X872, representative of mutants which are missing UDP-glucose, UDP-glucuronic acid, and UDP-galacturonic acid (class 1). Spectra of peaks eluting in the regions of interest are shown for comparison with those in FIG. 2.

FIG. 4 depicts a chromatogram of a cell extract from strain X869, representative of mutants which are missing GDP-mannose (class 2). Spectra of peaks eluting in the regions of interest are shown for comparison with those in FIG. 2.

FIG. 5 depicts a chromatogram of a cell extract from strain X871, representative of mutants which are missing UDP-glucuronic acid and UDP-galacturonic acid (class 3). Spectra of peaks eluting in the regions of interest are shown for comparison with those in FIG. 2.

FIG. 6 depicts a chromatogram of cell extract X866, representative of mutants which are missing UDP-glucose, GDP-mannose, UDP-glucuronic acid and UDP-galacturonic acid (class 4). Spectra of peaks eluting in the regions of interest are shown for comparison with those in FIG. 2.

FIG. 7 shows the steps in the construction of plasmid pTS13, which complements the defect preventing synthesis of UDP-glucose and UDP-glucuronic acid in mutant X649 (class 1).

FIG. 8 shows the steps in the construction of plasmid pAS9, which complements the defect preventing synthesis of UDP-glucuronic acid in mutant X736 (class 3).

FIG. 9 shows the steps in the construction of plasmid pAS7, which complements defects preventing the synthesis of UDP-glucose, GDP-mannose and UDP-glucuronic acid in mutant X652 (class 4), and defects preventing the synthesis of GDP-mannose in mutants X711 and X712 (class 2).

FIG. 10 depicts a chromatogram of a cell extract from *Paracoccus denitrificans,* showing the presence of UDP-glucose and GDP-mannose, but not UDP-glucuronic acid.

FIG. 11 depicts spectra verifying the identification of UDP-glucose and other uridine-containing compounds in the cell extract of *Paracoccus denitrificans* shown in FIG. 10.

FIG. 12 depicts spectra verifying the identification of GDP-mannose in the cell extract of *Paracoccus denitrificans* shown in FIG. 10, and indicating that late-eluting compounds observed in the figure are adenosine-containing compounds.

DETAILED DESCRIPTION OF THE PREFERRED EMBODIMENTS

The present invention relates generally to the synthesis, using recombinant-DNA methods, of various sugar nucleotides. The following detailed description uses, by way of example, a description of the production of UDP-glucose, GDP-mannose and UDP-glucuronic acid useful in part in the production of xanthan gum and variants thereof.

The sugar nucleotides UDP-glucose, GDP-mannose and UDP-glucuronic acid are direct precursors in the biosynthetic pathway for xanthan gum. Addition of all of these compounds is required to detect in vitro xanthan biosynthesis as described by Vanderslice et al., supra, specifically incorporated herein by reference. Because of the specificity of sugar transferases, other sugar nucleotides such as ADP-glucose cannot serve as precursors to xanthan. The pathways for synthesis of the three required sugar nucleotides in *X. campestris* are presented in FIG. 1. *Xanthomonas campestris* does not have detectable concentrations of UDP-galactose, so that the glucose-1-phosphate-UDP-galactose uridyl transferase reaction observed in other bacteria such as *E. coli* cannot occur.

Mutant strains of *X. campestris,* unable to make xanthan gum in vivo (Gum− strains), can be divided into two classes, based on the ability of cell lysates to synthesize xanthan in vitro when supplied with UDP-glucose, GDP-mannose and UDP-glucuronic acid. Mutants unable to make xanthan in vitro are defective in the xanthan biosynthetic machinery (sugar transferases and polymerase). Those able to make xanthan in vitro when supplied with exogenous substrates are deficient in the ability to make the required precursors in vivo. Some of this second class of mutants include those defective in glucose transport and metabolism itself, where the rate of xanthan synthesis is very low. Others, described below, have the normal complement of catabolic enzymes, but are lacking enzymes required to synthesize one or more of the sugar nucleotides themselves.

Such mutants have been obtained by picking Gum− colonies after transposon mutagenesis of *X. campestris* and analyzing in vitro xanthan biosynthesis in the presence of added UDP-glucose, GDP-mannose, and UDP-glucuronic acid. The specific sugar nucleotide defects have been identified in vivo by extraction of the sugar nucleotides and analysis of extracts using high performance liquid chromatography procedures. Four mutant classes have been identified. These include those defective in synthesis of UDP-glucose, UDP-glucuronic acid and other sugar nucleotides derived from these compounds; 2) those defective in synthesis of GDP-mannose and related compounds; 3) those defective in synthesis of UDP-glucuronate and related compounds, but not UDP-glucose; and 4) those defective in synthesis of UDP-glucose, UDP-glucuronic acid, GDP-mannose, and related compounds. Mutant class 3 is clearly defective in UDP-glucose dehydrogenase, since conversion of UDP-glucose to UDP-glucuronic acid is a single step process. The other mutant classes have been characterized by analysis of in vitro enzyme activities required for sugar nucleotide biosynthesis.

Glucose-6-phosphate and fructose-6-phosphate are key inter-mediates in microbial metabolism. The pathway from fructose-6-phosphate to UDP-N-acetyl glucosamine is common to Gram negative and Gram positive bacteria. UDP-N-acetyl glucosamine is an essential precursor of peptidoglycan in the cell wall. The two pyrophosphorylases depicted as 4 and 12 in FIG. 1, are the committed steps in biosynthesis of UDP-glucose and GDP-mannose; in other organisms glucose-1-phosphate can react with other nucleotide triphosphates to form other sugar nucleotides, e.g., ADP-glucose and TDP-glucose. In the UDP-glucose pathway, the gene for UDP-glucose pyrophosphorylase, as described in Example 4 has been isolated. Mutations in this gene prevent synthesis not only of UDP-glucose but also of the other sugar nucleotides derived from it, viz. UDP-glucuronic acid and UDP-galacturonic acid. The gene for UDP-glucose dehydrogenase (enzyme 5) has also been isolated as set forth in Example 5. Mutations in this gene prevent synthesis of UDP-glucuronic acid and sugar nucleotides derived from it, viz. UDP-galacturonic acid. Such polar effects consequently disrupt not only xanthan biosynthesis but also lipopolysaccharide synthesis in *X. campestris* by disrupting the supply of sugar nucleotides for that process.

In addition, mutants deficient in the synthesis of GDP-mannose have been found. These mutants grow normally on mannose, and so possess enzyme 2, phosphomannose isomerase, an enzyme commonly found in bacteria. Consequently, they must be deficient in enzymes 11 and/or 12 as described in Example 9. Cross-hybridization mapping and restriction maps indicate these mutations occur in at least two separable sites within the *X. campestris* chromosome. A plasmid has been developed which promotes synthesis of GDP-mannose when inserted into these mutants.

The details of this plasmid are set forth in Example 6. In addition, this plasmid complements the Gum− defect of a mutant unable to make phosphoglucomutase (pgm) as well as GDP-mannose. This mutation may be in a regulatory gene controlling expression of pgm or it may be in the pgm structural gene itself.

Another mutant, X872, defective only in phosphoglucomutase, has been found. By the procedures described herein, one of ordinary skill in the art, in light of the current state of the applicable science, can construct a plasmid carrying a wild-type copy of this gene.

Thus, the genes for the synthesis of the immediate xanthan precursors have been identified by the present inventors. These genes include the genes for enzymes required for synthesis of UDP-glucose, GDP-mannose and UDP-glucuronic acid. Plasmids containing wild-type copies of the genes encoding the enzymes have been obtained from a genomic library constructed in the phage lambda. $^{32}$P-Labeled plasmid DNA of recombinant plasmids consisting of the vector RSF1010 carrying a cloned DNA segment of chromosomal DNA from a transposon-induced sugar nucleotide defective mutant has been identified. The cloned fragment contains the transposon and flanking chromosomal DNA. Such recombinants are readily isolated as described by Capage et al., supra. Three multicopy broad host range plasmids have been constructed using standard techniques as described more fully in the Examples below. These plasmids, pTS13, pAS7 and pAS9, contain DNA which complements strains from mutant classes 1, 2, and 3, respectively, as described above. In addition, plasmid pAS7 complements a mutant from class 4. None of these plasmids cross-hybridize with DNA within or flanking the region containing the xanthan biosynthetic genes themselves. Two different mutant loci have been identified in plasmid pAS7 by cross-hybridization of lambda phage, restriction fragment analysis and genetic complementation. Construction of the plasmids and additional information is provided in FIGS. 7 through 9, discussed in more detail in the Examples below.

Each plasmid, when inserted into mutants in the appropriate complementation group, restores the ability of the mutants to produce xanthan gum, as denoted by the mucoid appearance of the resultant colonies. In addition, sugar nucleotides have been examined in extracts from the complemented strains to insure that the plasmids have restored the missing biosynthetic ability. Plasmid pTS13 most apparently carries the gene for UDP-glucose pyrophosphorylase, since mutant X649 is unable to make UDP-glucose but has wild-type amounts of phosphoglucomutase. Furthermore, plasmid pTS13 when inserted into mutants derived from X649 confers the ability to make UDP-glucose pyrophosphorylase (Example 8). The strain grows normally on glucose so it is not defective in synthesis of glucose-6-phosphate, a key intermediate in utilization of glucose for growth.

As noted above, there is an absolute requirement for UDP-glucose, GDP-mannose and UDP-glucuronic acid in order for bacteria to synthesize xantham gum. Although modification of xanthan by acetylation and pyruvylation, requiring acetyl-coenzyme A and phosphoenolpyruvate, respectively, as precursors, affects Theological properties of the gum, acetylation or pyruvylation is not required for its biosynthesis. In addition, both of these latter precursors are essential components of bacterial metabolism. UDP-glucose, GDP-mannose, and UDP-glucuronic acid are common sugar nucleotides in certain bacteria, but not all bacteria have them all or have them in quantities sufficient to support xanthan synthesis. Expression of the xanthan biosynthetic pathway in organisms other than *X. campestris* requires that the sugar nucleotide precursors are synthesized in such alternative hosts, preferably at rates sufficient to support economic production of xanthan gum. Several alternative hosts have been identified which have little or no UDP-glucuronic acid (See Example 7). Insertion of DNA carrying the gene for UDP-glucose dehydrogenase into such a strain would be essential to obtain xanthan synthesis at a high rate.

The basic requirements for expression of sugar nucleotide biosynthetic genes in alternative hosts are similar to those in *X. campestris* mutants. The gene or genes required must be inserted into the host in a fashion so that they can be stably maintained, whether by integration into the chromosome or maintenance on a plasmid. The gene construct must be such that the host will synthesize the appropriate mRNA and translate it into a functional protein, which preferably will be relatively stable in the new host. In addition, the host must be able to provide the substrates and cofactors required for synthesis of the sugar nucleotide itself.

Both high and low copy number plasmids exist which have broad host ranges. Insertion of the appropriate sugar nucleotide biosynthetic genes onto plasmids has already occurred. Transformation or conjugation can be used to introduce such plasmids into alternative hosts in a fashion similar to that by which the plasmids were transferred from *E. coli* to mutant *X. campestris* strains. These broad host range plasmids generally will infect Gram negative bacteria. Shuttle vectors exist by which the *X. campestris* genes can be transferred to Gram positive bacteria, if desired. Insertion of the plasmids and maintenance can be verified by standard procedures.

Expression of the genes in alternative hosts can be monitored in several ways: the mRNA transcribed from the gene can be detected by hybridization; the protein itself can be detected by immunoassay or functional assay; and the sugar nucleotide previously missing can be identified by established chromatographic procedures. Analysis by one or several of these techniques, as required, should permit adjustments in the gene construct to optimize expression.

The intracellular environment of alternative hosts will likely be similar to that of *X. campestris,* particularly if similar external environments are maintained—e.g. pH and temperature, It is known from in vivo studies with *X. campestris* that xanthan biosynthesis takes place over a broad temperature range. i.e., 12° to 37° C., though the rate is maximal between 27° and 30° C. Clearly, the enzymes responsible for synthesis of the sugar nucleotide precursors must be functional within this range. Initial analyses would be conducted at 27° to 30° C.

It is to be understood that broad application of the teachings of the present invention to the production of specific sugar nucleotides in various hosts will be within the capabilities of one having ordinary skill in the art in light of the teachings contained herein. Thus, the following Examples are illustrative only and are not restrictive of the invention, as claimed.

EXAMPLE 1

This example discusses the specific sugar nucleotide defects identified in various *X. campestris* strains that are Gum− in vivo.

The initial collection of mutants defective in sugar nucleotide synthesis was obtained from *X. campestris* strains unable to make xanthan in vivo after transposon mutagenesis, as described in Capage et al., supra. Several Gum− strains were able to make xanthan in vitro when supplied with the sugar nucleotides UDP-glucose, GDP-mannose, and UDP-glucuronic acid. These mutants were defective in sugar nucleotide synthesis, rather than biosynthesis of xanthan itself. Subsequently, such mutants were found to be sensitive to the dye toluidine blue. Additional sugar nucleotide mutants were obtained by screening other Gum− strains for toluidine blue sensitivity. These strains proved to be resistant to some virulent phage which killed wild-type *X. campestris* and Gum− mutants defective in xanthan biosynthesis itself.

The following method was employed to identify the specific sugar nucleotide defects in strains which were Gum+ in vitro but Gum− in vivo. An isolated colony from each strain was picked and inoculated into 10 ml YM broth (3 g yeast extract, 3 g malt extract and 5 g peptone per liter) with 2% glucose in a 125 ml Erlenmeyer flask. Cultures were incubated at 30° C., 250 rpm, for 24 hours or until turbid. Five percent inocula were transferred from YM broth into modified PACE medium (5 g $KH_2PO_4$, 5 g $K_2HPO_4$. 0.2 g $MgSO_4.7H_2O$, 0.53 g $(NH_4)_2SO_4$, 0.006 g $H_3BO_3$, 0.006 g $ZnCl_2$, 0.003 g $FeCl_3.6H_2O$ and 0.02 g $CaCl_2$ per liter, pH 7.0) with glucose as the carbon source and allowed to grow at 30° C. for 24 hours. Cultures were harvested by centrifugation, washed twice with PACE salts, and resuspended in a volume of PACE sufficient to give an absorbance at 600 nm of 100. Samples, 1.5 ml, were placed in 50 ml Erlenmeyer flasks containing sufficient glucose to bring the concentration to 20 mM. Each sample was incubated in a 30° C. water bath at 400 rpm for ten minutes, then 1 ml was removed and added to 0.1 ml of 11 N formic acid in an Eppendorf centrifuge tube. The tube was capped, the contents mixed for 5 seconds on a vortex mixer, then the tube was placed in a dry ice-alcohol bath. After all samples had been processed, the tubes were removed from the dry ice bath, thawed at room temperature, and centrifuged for 5 minutes to pellet the cell debris. The supernatants were placed in prechilled 15 ml conical centrifuge tubes and frozen in a dry ice-alcohol bath again. Frozen samples were placed on a lyophilizer and taken to dryness. The contents of each tube were dissolved in 0.2 ml HPLC buffer, composed of 40 mM phosphoric acid adjusted to pH 6.5 with triethylamine (Aldrich). Samples were filtered through 0.45 um filters into microsample vials, then analyzed by injection onto a 4.6 mm×250 mm C18 reverse phase ion pair column, 40° C., flow rate of 0.8 ml per minute. Sugar nucleotides were identified by comparing retention times to those of standards run under the same conditions (FIG. 2), and by examining the spectra of compounds eluting in the region of interest.

Four classes of sugar nucleotide mutants were identified using this procedure:

(1) mutants unable to synthesize UDP-glucose and UDP-glucuronic acid;

(2) mutants unable to synthesize GDP-mannose;

(3) mutants able to synthesize UDP-glucose but not UDP-glucuronic acid; and (4) mutants unable to synthesize UDP-glucose, GDP-mannose, and UDP-glucuronic acid.

Representative chromatograms and spectra of standards for each mutant class are shown in FIGS. 2 through 6. Mutants in classes 1, 3, and 4 also did not synthesize UDP-galacturonic acid, a *X. campestris* lipopolysaccharide precursor. Based on these data, *X. campestris* must make UDP-galacturonic acid from UDP-glucuronic acid.

Extracts from wild-type strains of *X. campestris* had all of the sugar nucleotides required for xanthan biosynthesis. Gum− mutants defective in the xanthan biosynthetic pathway itself had higher concentrations of the precursor sugar nucleotides than did wild-type cells as set forth in Table 1.

TABLE 1

Relative amounts of UDP-glucose; GDP-mannose, and UDP-glucuronic acid in wild-type *X. campestris* and mutants deficient in the xanthan biosynthetic enzymes themselves.

|  | UDP-glucose | GDP-mannose | UDP-glucuronic acid |
|---|---|---|---|
| *X. campestris* S4-L | 1.0 | 1.0 | 1.0 |
| *X. campestris* X648 | 2.5 | 4.7 | 2.0 |
| *X. campestris* X655 | 3.5 | 5.4 | 1.9 |
| *X. campestris* X705 | 4.2 | 7.1 | 2.0 |

These data indicate that the rate of xanthan synthesis in wild-type cultures may be limited by the supply of precursor sugar nucleotides.

EXAMPLE 2

This example describes phosphoglucomutase activity in *X. campestris* transposon-induced mutants defective in sugar nucleotide synthesis.

Cytoplasmic and membrane fractions were prepared from the transposon mutants previously found to be defective in sugar nucleotide synthesis. Extracts of *X. campestris* S4-L, NRRL, B1459, were also prepared to serve as positive controls. Cultures were transferred from isolated colonies on plates to 5 ml YM broth with 1% glucose and grown on a tube roller into stationary phase. Duplicate 500 ml flasks containing 100 ml YT (8 g tryptone, 5 g yeast extract and 5 g NaCl per liter) broth with 1% glucose were inoculated with 2 ml of culture and placed on a shaker at 300 rpm in a 30° C. incubator. After 24 hours the cultures were combined and centrifuged. The cell pellets were washed twice in 100 ml phosphate-buffered saline, pH 7.2, then resuspended to 20% wet weight to volume in 50 mM MOPS buffer, pH 7.2, containing 10 mM $MgCl_2$. This procedure was used to remove residual culture medium from the cells. The cell suspensions were disrupted by passage twice through a French pressure cell operated at 15,000 psi. Lysates were treated with DNAase to reduce viscosity, then centrifuged at 2,500×g to remove unbroken cells and debris. The supernatants were carefully removed with a Pasteur pipette, then separated into cytoplasmic and membrane fractions by centrifugation in a swinging bucket rotor at an average centrifugal force of 130,000×g. The supernatants containing the cytoplasmic contents were decanted and frozen at –70° C. Each membrane-containing pellet was resuspended in 1.0 ml of MOPS $MgCl_2$ buffer, then also frozen at –70° C. Enzymes required for sugar nucleotide synthesis are normally found in the cytoplasmic contents. Separation of the cytoplasmic contents from the cell membranes facilitates enzymatic assays coupled to reduction of NADP. NADPH oxidase is a membrane-bound enzyme, and unless removed or inactivated can rapidly reoxidize the reduced pyridine nucleotides whose accumulation is used to follow the reactions.

The protein concentration in each cytoplasmic extract was determined using the procedure of Lowry et al., J. Biol. Chem. 193:265–275 (1951), specifically incorporated herein by reference, with bovine serum albumen as the standard. The activity of glucose-6-phosphate dehydrogenase in each extract was measured by following the increase in absorbance at 340 nm due to the accumulation of NADPH produced during the oxidation of glucose-6-phosphate to 6-phosphogluconate. This enzyme is a key enzyme in the metabolism of glucose by *X. campestris,* and served as an internal control. Reaction conditions are described in a footnote to Table 2.

Phosphoglucomutase, which converts glucose-6-phosphate to glucose-1-phosphate, the direct precursor of UDP-glucose, was also assayed in the cytoplasmic fractions. The mutase activity is reversible, so glucose-1-phosphate was used as the substrate. In addition, purified glucose-6-phosphate dehydrogenase purchased from Sigma Chemical Co. was added to the reaction mixture in excess. The rate of formation of NADPH is a measure of the rate at which glucose-6-phosphate was formed by phosphoglucomutase present in the extracts. Reaction conditions and results of the assay are summarized in Table 2.

TABLE 2

Glucose-6-phosphate dehydrogenase (G6PD) and phosphoglucomutase (PGM) activity in cytoplasmic extracts of Transposon-induced sugar nucleotide mutants of *X. campestris*. Enzyme activities are expressed as nmol/min/mg protein.

| Strain | UDPglc | GDPman | UDPglcA | G6PD[a] | PGM[b] |
|---|---|---|---|---|---|
| S4-L | + | + | + | 268 | 238 |
| X649 | – | + | + | 182 | 411 |
| X652 | – | – | – | 255 | 2 |
| X711 | + | – | + | 144 | 191 |
| X712 | + | – | + | 154 | 223 |
| X736 | + | + | – | 184 | 496 |
| X826 | + | + | – | 154 | 276 |
| X871 | + | + | – | 97 | 348 |
| X828 | – | – | – | 148 | 7 |
| X866 | – | – | – | 151 | 1 |
| X869 | + | – | + | 163 | 535 |
| X872[c] | – | + | – | 104 | 2 |

[a]The reaction was started by adding 0.05 ml cytoplasmic fraction, approximately 10 mg/ml protein. The reaction mixture contained 40 mM Tris HCl, pH 8.6, 5 mM glucose-6-phosphate, 1.6 mM NADP, and 15 mM $MgCl_2$ in 1.0 ml total volume.
[b]Reaction conditions as for G6PD, but glucose-1-phosphate, was used instead of glucose-6-phosphate. The reaction mixture also contained 1 mM dithiothreitol, 0.2 mM glucose-1,6-diphosphate, and approximately 10 units G6PD from Sigma Chemical Company.
[c]Deposited at ATCC Accession No. 53471

All extracts had significant activities of glucose-6-phosphate dehydrogenase, ranging from 97 to 268 nmol/min/mg protein. Phosphoglucomutase activity was 191 nmol/ min/mg protein or higher in all extracts prepared from mutants capable of synthesizing UDP-glucose. Extracts from all mutants except X649 that were unable to synthesize UDP-glucose (X828, X652, X866, and X872) had little or no phosphoglucomutase activity. Such a defect is sufficient to prevent synthesis of UDP-glucose.

Strain X649 is unable to make the UDP-glucose family of sugar nucleotides. Phenotypically, it resembles the Tn903 mutant, strain X872. However, X649 has normal phosphoglucomutase activity, whereas strain X872 is defective in this enzyme. Strain X649 must be defective in the UDP-glucose pyrophosphorylase itself.

Strain X652 is unable to make the UDP-glucose and GDP-mannose families of sugar nucleotides. Like the Tn903 mutants X828 and X866 which lack these sugar nucleotides, X652 has little or no phosphoglucomutase activity. Mutants defective in GDP-mannose synthesis alone—strains X657, X711, X712 and X869—have normal phosphoglucomutase activity. Strains X736, X826 and X871 are unable to make UDP-glucuronic acid. They also have normal phosphoglucomutase activity.

EXAMPLE 3

This example describes the method for mapping sugar nucleotide defects in Tn10-Induced mutants Plasmid probes were obtained for all Tn10-induced mutants defective in sugar nucleotide metabolism by cloning Tn10 plus flanking chromosomal sequences from each mutant. A lambda bank was probed to obtain lambda recombinants which hybridized to each probe but carried segments of *X. campestris* wild-type DNA. These phage were plaque-purified and used to map the sugar nucleotide mutations by cross hybridization to the plasmid probes containing Tn10 and flanking DNA.

None of the sugar nucleotide probes mapped within the DNA region containing genes for the xanthan biosynthetic pathway itself. Phage containing wild-type DNA for mutant X649 did not hybridize to any other sugar nucleotide probes. Similarly, phage containing wild type DNA from the region of the Tn10 insertion in mutant X736 DNA did not hybridize to other sugar nucleotide probes. The defective genes in these strains thus are not linked to the other sugar nucleotide genes.

Plasmids pTX652, pTX657, pTX711 and pTX712 hybridized to an overlapping set of recombinant lambda phages containing cloned *X. campestris* DNA. Plasmid pTX711 hybridized to some, but not all, of the lambda phage which hybridized to pTX652, pTX657 and pTX712.

Association of the mutation in strain X652 with mutations preventing synthesis of GDP-mannose was unexpected since X652 also cannot make UDP-glucose or UDP-glucuronic acid. The mutation in X652 may be in a trans-acting regulatory gene affecting synthesis of UDP-glucose and GDP-mannose, or in a structural gene encoding an enzyme essential for UDP-glucose synthesis, but exerting a polar effect on expression of the GDP-mannose genes.

EXAMPLE 4

This example demonstrates complementation of the mutation in strain X649 by plasmid pTS13

All sugar nucleotide mutants were obtained by transposon mutagenesis. A lambda library of *X. campestris* genomic DNA was probed with plasmid pTX649 derived from cloning the transposon Tn10 plus flanking chromosomal sequences from the mutant X649 (as described in Capage et al., supra.), which is defective in synthesis of UDP-glucose and UDP-glucuronic acid. Ten lambda recombinants were identified that hybridized to the pTX649 probe. These phage were plaque-purified.

Restriction digests and gel electrophoresis was performed on the DNA of each lambda clone. In these digestion patterns, the wild type fragment of *X. campestris* DNA that is mutated in strain X649 was identified. This 6.5 kb PstI fragment has been purified by electroelution from preparative agarose gels. This PstI fragment was cloned into the PstI site of pBR322 to make plasmid pTf6.5. Another plasmid was constructed by digesting pTf6.5 and plasmid RSF1010 with EcoRI, then ligating both plasmids together. Hybrid plasmids were selected by ability to confer streptomycin and tetracycline resistance to *E. coli* after transformation. This chimeric plasmid, pTS13, contains the 6.5 kb PstI fragment (FIG. 7).

The plasmid was then transferred to *X. campestris* strain X649 by a triparental conjugal transfer directed by pRK2013.

The cloned 6.5 kb fragment carried by pTS13 does complement mutant X649. When the mating mixture of the pTS13 transfer into X649 was plated on rif and strep, all of the colonies were Gum+ and not distinguishable from wild type. Three Gum+ exoconjugants were analyzed and showed that they did contain the plasmid. Furthermore, a plasmid "curing" experiment was performed. In this experiment, X649 (pTS13) was grown up under conditions which promote loss of plasmids and then plated out in the absence of any drugs that would select the plasmid. In several experiments, significant frequencies (10–50%) of Gum– colonies were observed in such platings. Three such Gum– isolates were examined and showed that the plasmid pTS13 had been lost. However, three Gum+ isolates from such an experiment were all found to retain pTS13. The correlation between presence of the plasmid and the Gum+ phenotype argues that the initial Gum+ property is not due to recombination but rather to expression of the plasmid-borne gene.

Extracts were made from strains X649 and X649 containing pTS13. The extract from X649 with the plasmid had UDP-glucose, as determined by spectral analysis and retention time. The extract from X649 alone did not.

Since extracts from X649 have normal amounts of phosphoglucomutase (Example 1), the enzyme defect which prevents synthesis of UDP-glucose must be located in the gene coding for UDP-glucose pyrophosphorylase, which is contained on plasmid pTS13. Because this plasmid is a chimera of RSF1010, it can be transferred to Gram negative bacteria other than *X. campestris,* and confer on them the ability to make UDP-glucose if they have the ability to make glucose-1-phosphate.

EXAMPLE 5

This example demonstrates complementation of the mutation in strain X736 by plasmid pAS9.

A set of 5 recombinant lambda phages were isolated that contained chromosomal *X. campestris* DNA from the region of the Tn10 insertion in X736. These phages were isolated from the lambda gene bank by screening for recombinant phages that hybridized to plasmid pTX736. Plasmid pTX736 consists of the PstI fragment of chromosomal DNA from mutant X736 that contains the Tn10 insertion causing the mutant phenotype, cloned into plasmid vector RSF1010.

Figure 8:
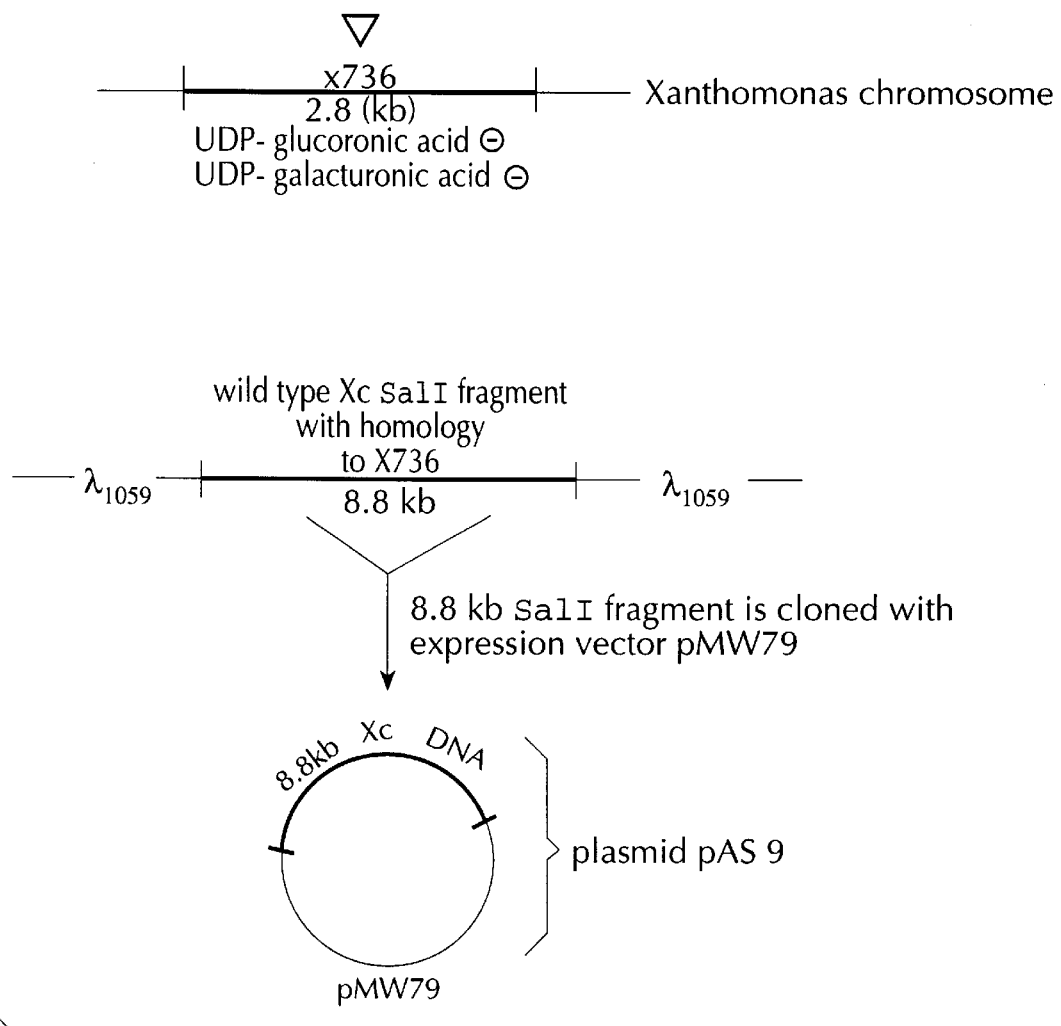

These lambda 736(+) phages were screened by Southern blot hybridization to identify relatively large DNA segments that contained the wild-type PstI fragment of interest. The DNA's from the lambda recombinants were digested with several restriction endonucleases and run out on agarose gels along with a control of wild-type chromosomal DNA cut with the same set of enzymes. The digests were then probed with radiolabeled pTX736 plasmid DNA. SalI digests of several different lambda 736(+) isolates generated a fragment of 9 kb that hybridized to the probe. The SalI digest of wild-type chromosomal DNA also produced a band of 9 kb that annealed to the probe. Because the lambda 736 recombinants produced relatively few SalI fragments, a shotgun cloning from lambda into pMW79 was performed. The plasmid vector pMW79 contains a unique SalI site that lies within the tetracycline-resistance gene. Therefore, both pMW79 and lambda 736(+) DNA were digested with SalI and the digestion products were ligated together. The ligation reaction was used to transform *E. coli,* ampicillin-resistant transformants were selected, and 650 of these were then tested for sensitivity to tetracycline in order to identify recombinant plasmids. Ten $Amp^r$ $Tet^s$ isolates were found. Plasmid DNA was extracted from these transformants and analyzed by restriction endonuclease digestion and agarose gel electrophoresis. The recombinant of interest was found. This plasmid, containing the cloned 9 kb SalI fragment, was designated pAS9. (FIG. 8).

This plasmid was transferred into *X. campestris* to look for complementation of the X736 Gum– defect. Plasmid pAS9 was mobilized into a rifampicin-resistant derivative of X736, designated X1017, and the Rif$^r$ wild-type (Gum+) strain X77. These mobilizations were performed as standard triparental conjugal transfers directed by pRK2013. *X. campestris* conjugants carrying the plasmid of interest were selected by plating on rifampicin (to select against the *E. coli* donor and mobilizer strains) and streptomycin (to select for the presence of pAS9). The Rif$^r$ and Strep$^r$ progeny of the mating of pAS9 into X1017 were exclusively Gum+. Three Gum+ derivatives were chosen and examined for plasmid. It was found that all three clearly contained the plasmid pAS9 and that the plasmid had not undergone any obvious rearrangement, as determined by restriction endonuclease digestions. Furthermore, a plasmid "curing" experiment was performed. In this experiment, X1017 pAS9 was grown up under conditions which promote loss of plasmids and then plated out in the absence of any drugs that would select for the plasmid. Significant frequencies of Gum– colonies were observed in such platings. Three such Gum– isolates were examined and it was found that plasmid pAS9 had been lost. However, three Gum+ isolates from such experiment were all found to retain pAS9. The correlation between presence of the plasmid and the Gum+ phenotype argues that the Gum+ property is not due to recombination but rather to expression of the plasmid-borne gene.

Since mutant X736 can produce UDP-glucose but not UDP-glucuronic acid, it most certainly is defective in the single enzyme UDP-glucose dehydrogenase responsible for the conversion of UDP-glucose to UDP-glucuronic acid. The gene for this enzyme is contained on plasmid pAS9.

EXAMPLE 6

This example demonstrates complementation of the mutations in strains X652, X711 and X712 by plasmid pAS7.

A lambda library of *X. campestris* genomic DNA was probed with plasmid pTX652 derived by cloning the transposon Tn10 plus flanking chromosomal sequences from the sugar nucleotide mutant X652 into plasmid RSF1010. Mutant X652 does not make UDP-glucose, GDP-mannose or UDP-glucuronic acid. Recombinant phage which hybridized to pTX652 were plaque-purified. Southern blots of restriction digests of these phage, probed with pTX652, identified a 9kb BamHI fragment which contained wild-type sequence corresponding to the site of the transposon insertion. This 9kb BamHI fragment was purified and ligated into the BamHI site of plasmid pMW79. The ligation mixture was used to transform *E. coli*, and ampicillin-resistant transformants were selected. These were screened for sensitivity to tetracycline; insertion of foreign DNA into the BamHI site of pMW79 will inactivate the gene encoding resistance to tetracycline. Plasmid pAS7 containing the 9kb BamHI fragment was obtained by this procedure (FIG. 9).

The plasmid was then transferred to *X. campestris* strain X1043 from *E. coli* by a triparental conjugal transfer directed by pRK2013. *X. campestris* X1043 was obtained by mating pTX652 into *X. campestris* strain X77 (a rifampicin-resistant mutant obtained from *X. campestris* NRRL B1459 S4-L) and forcing homologous recombination by imposing tetracycline selection. The different antibiotic resistance of X1043 from X652 facilitated counter-selection against the *E. coli* donor in subsequent matings. After transfer of plasmid pAS7, X1043 was restored to a Gum+ phenotype. This phenotype reverted to Gum– when the strain was cured of pAS7, indicating that the Gum+ phenotype was due to expression of the plasmid-borne copy of the chromosomal gene inactivated by transposon insertion in strain X652.

As shown in Example 3, the mutations in strains X652, X711 and X712 are clustered on the *X. campestris* chromosome. Plasmid pAS7 restored the gum+ phenotype upon transfer into mutants X711 and X712 by conjugation in a triparental mating. Complemented strains which lost the plasmid, became Gum–. Strains X711 and X712 are unable to synthesize GDP-mannose, as is strain X652. Plasmid pAS7 restores this ability, and so contains the gene(s) encoding the enzyme(s) required for synthesis of GDP-mannose.

Strain X652 is also deficient in UDP-glucose. This defect is consistent with the lack of phosphoglucomutase in strain X652 (Example 2). The same linkage group which contains genes coding for enzymes required for GDP-mannose biosynthesis, also contains the structural gene for phosphoglucomutase or a regulatory gene controlling expression of phosphoglucomutase.

EXAMPLE 7

This example describes sugar nucleotide pools in the alternative hosts.

Figure 10:
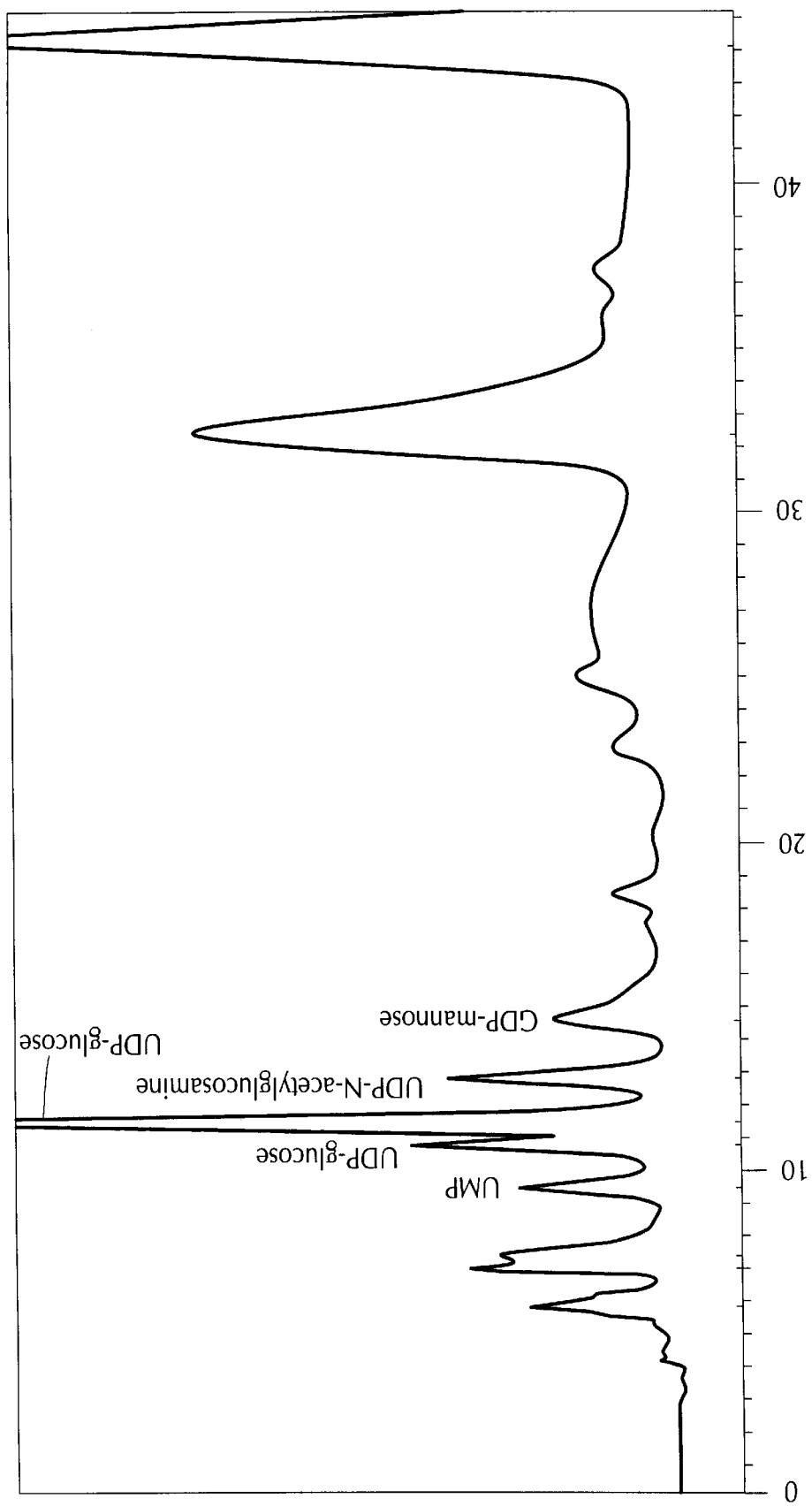
Figure 11:
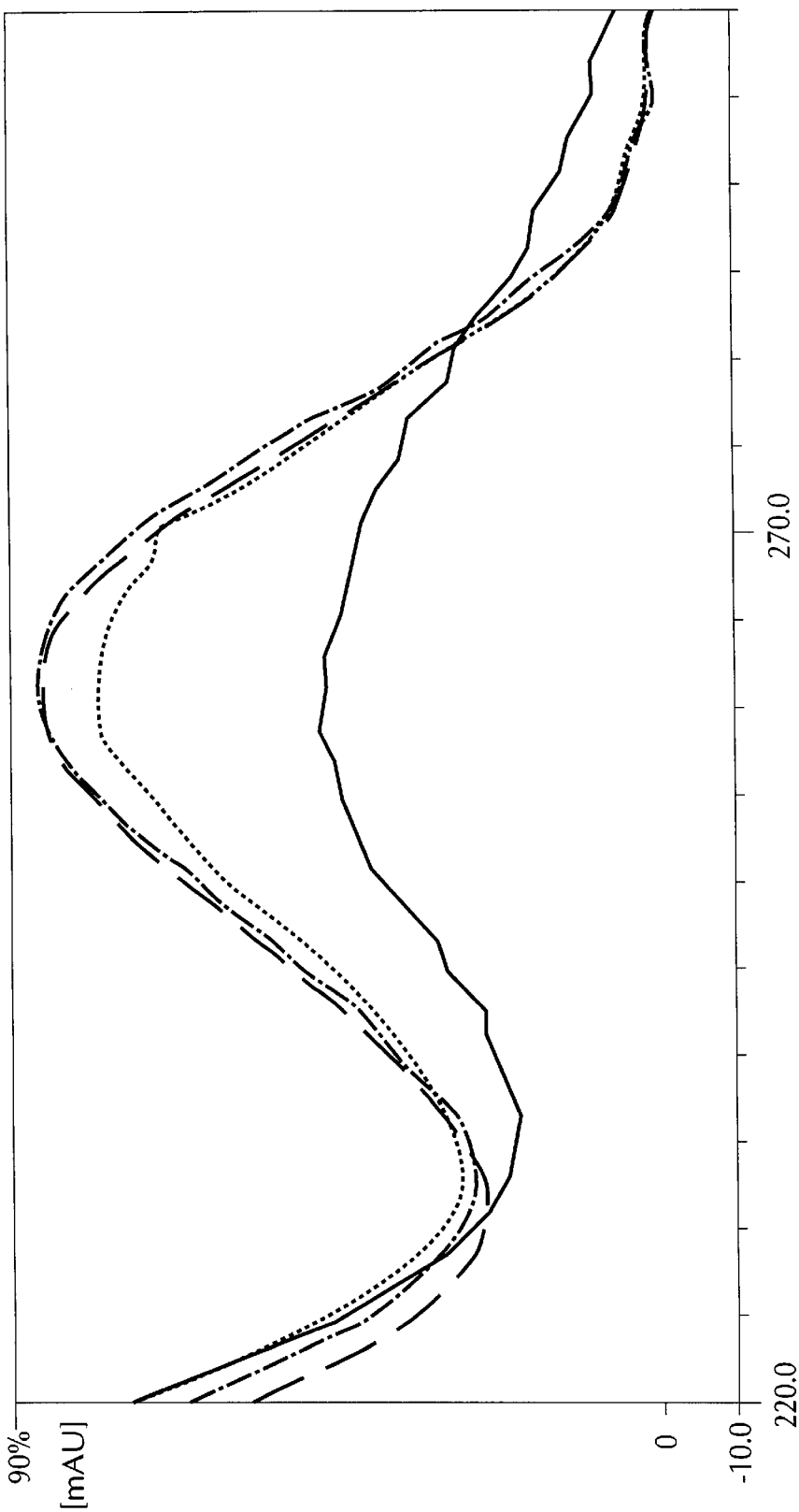
Figure 12:
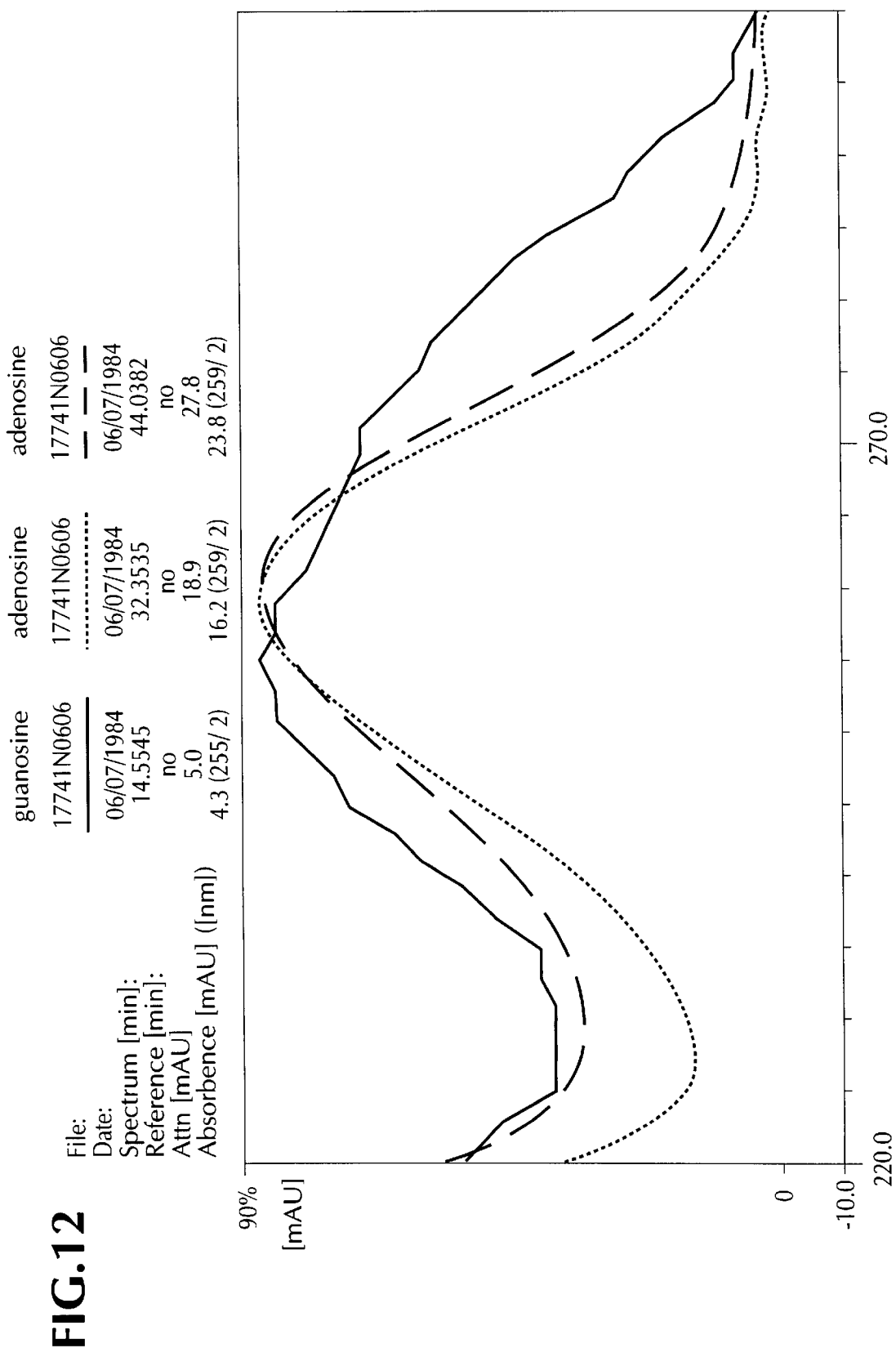

The sugar nucleotides in *Paracoccus denitrificans* (ATCC 17741), *Pseudomonas stutzeri* (ATCC 17588), and *Pseudomonas perfectomarina* (ATCC 14405) were analyzed using procedures developed for *X. campestris*. All organisms were grown for twelve hours with two percent glucose as the carbon source. Cells were collected, washed, and resuspended to an absorbance at 600 nm of 100. The cell pellets had a pink hue typical of denitrifying bacteria which have derepressed synthesis of the cytochromes required for anaerobic growth (a typical response to oxygen limitation during growth). Consequently, 25 mM nitrate was included as an additional electron acceptor in the incubation mixtures. Cell suspensions were incubated with 20 mM glucose for five minutes with and without nitrate, then extracted with formic acid as described in Example 1. Extracts were lyophilized, dissolved in TEA-phosphate buffer and analyzed by HPLC. *Paracoccus denitrificans* had UDP-glucose and GDP-mannose, but undetectable amounts of UDP-glucuronic acid, as verified by spectra of peaks in the regions of interest (FIGS. 10–12). Similarly, *Pseudomonas perfectomarina* and *Pseudomonas stutzeri* had UDP-glucose and GDP-mannose. UDP-glucuronic acid was not detected in extracts from either organism.

It is intended to insert plasmid pAS9, described in Example 5, into all three bacteria by conjugation from an *E. coli* donor in a triparental mating to correct the inability of these strains to synthesize UDP-glucuronic acid.

EXAMPLE 8

This example describes UDP-glucose pyrophosphorylase activity in *X. campestris* transposon-induced mutants defective in sugar nucleotide synthesis.

Strain X649 was unable to make UDP-glucose (Example 1) but had phosphoglucomutase activity (Example 2). The experiments described below demonstrate that the mutation in this strain affects UDP-glucose pyrophosphorylase activity, and that the gene for UDP-glucose pyrophosphorylase is contained on plasmid pTS13.

To facilitate analysis of UDP-glucose pyrophosphorylase activity, three streptomycin-sensitive, rifampicin-resistant strains that carried the Tn10 insertion of strain X649 were constructed. One such strain, X1023, was constructed by the gene replacement procedure described by Capage et al., supra. Two other strains, X1024 and X1025, were constructed by chromosome mobilization. Plasmid pTS13 which complements the sugar nucleotide defect of strain X649 (Example 4) was inserted into X1023, X1024 and X1025 to obtain strains X1041, X1039 and X1040, respectively. Also, plasmid pTS13 was inserted into the Gum+ rifampicin-resistant strain X77, to create strain X1052.

Cytoplasmic fractions were prepared as described in Example 2 from these strains and *X. campestris* X77, which served as a positive control. UDP-glucose pyrophosphorylase converts glucose-1-phosphate and UTP to UDP-glucose and pyrophosphate. The reaction is reversible. UDP-glucose pyrophosphorylase activity was measured by coupling formation of glucose-1-phosphate from UDP-glucose to reduction of NAD or NADP by adding phosphoglucomutase and glucose-6-phosphate dehydrogenase, as described by Lieberman et al., Proc. Natl. Acad. Sci. USA 65:625–632 (1970), specifically incorporated herein by reference. In these assays HEPES buffer was used instead of Tris, and sodium phosphate was omitted from the reaction mixture. Sodium fluoride (5 mM) was added to inhibit pyrophosphatase activity.

In an experiment where NAD was used, strain X1023 had UDP-glucose pyrophosphorylase activity of 5.4 nmol per mg protein per minute, less than 10% of the UDP-glucose pyrophosphorylase activity of wild-type strain X77, 72.2 nmol per mg per minute. Almost all of the increase in absorbance at 340 nm in the X1023 reaction mixture was due to competing reactions, rather than UDP-glucose pyrophosphorylase activity itself. Strain X1039 had UDPG pyrophosphorylase activity of 18.7 nmol per mg per minute, fourfold higher than activity in X1023. This result demonstrates that plasmid pTS13 carries the UDP-glucose pyrophosphorylase gene.

To verify that pTS13 carries the UDP-glucose pyrophosphorylase gene, additional experiments were carried out with the other mutants, using NADP as the electron acceptor. Results are summarized in Table 3. Results of multiple determinations at different extract concentractions are presented.

TABLE 3

UDP-glucose pyrophosphorylase activity in cytoplasmic fractions of *X. campestris*, expressed as nmol NADPH, formed per minute per mg protein.

| Strain | UDP-Glucose pyrophosphorylase |
|---|---|
| X77 | 6.74, 3.46, 3.18 |
| X1023 | 1.83 |
| X1024 | 1.12 |
| X1625 | 0.57 |
| X1040 | 23.0, 8.83 |
| X1041 | 41.1, 45.9, 42.6, 39.3 |
| X1052 | 40.3, 42.1, 43.8 |

Strains X1023, X1024 and X1025 had little or no pyrophosphorylase activity. Strains X1040 and X1041, containing the plasmid complementing the defect in strains X1025 and X1023, had high activity. Similarly, strain X1052 had much higher activity than the wild-type parent, X77, without plasmid pTS13. Because pTS13 is derived from plasmid RSF1010, a high copy number plasmid, this difference in activity may reflect a gene dosage effect. Cytoplasmic extracts of strains X77 and X1040 were prepare again and assayed immediately for pyrophosphorylase activity, this time in a spectrophotometer equipped with a constant temperature sample compartment. The specific activities were 149 and 53.4 nmol per mg protein per minute for X77 and X1040, respectively.

These results confirm that the mutation in X649 prevents UDP-glucose synthesis by eliminating UDP-glucose pyrophosphorylase activity. This activity can be restored by plasmid pTS13, which must carry the gene for UDP-glucose pyrophosphorylase.

UDP-glucose pyrophosphorylase activity was also measured in cytoplasmic extracts from the Tn903 series of sugar nucleotide mutants. Reaction mixtures did not include NaF. Results are presented in Table 4.

TABLE 4

UDP-glucose pyrophosphorylase activity (UDPG PPase, expressed as nmol per minute per mg protein) in extracts of Tn903 sugar nucleotide mutants previously assayed for phosphoglucomutase activity (PGM).

| Strain | Missing Sugar Nucleotides | UDPG PPase |
|---|---|---|
| X77 | | 9.4 |
| X826 | UDP-GlcA | 10.5 |
| X871 | UDP-GlcA | 31.1 |
| X828 | UDP-Glc, UDP-GlcA, GDP-man | 28.5 |
| X866 | UDP-Glc, UDP-GlcA, GDP-man | 17.3 |
| X869 | GDP-Man | 5.88 |
| X872 | UDP-Glc, UDP-GlcA | 86.2 |

All strains had measurable pyrophosphorylase activity. The absence of phosphoglucomutase activity is sufficient to account for the inability of strains X828, X866, and X872 to synthesize UDP-glucose.

EXAMPLE 9

This example describes phosphomannomutase activity in *X. campestris* transposon-induced mutuants defective in sugar nucleotide synthesis.

Cytoplasmic extracts from previously identified sugar nucleotide mutants (Example 1) were prepared as described in Example 2. These extracts were assayed for phosphomannomutase (PMM), the enzyme that converts mannose-6-phosphate to mannose-1-phosphate, a substrate for GDP-mannose pyrophosphorylase. The enzyme activity is reversible. The assay (Table 5) was adapted from that of Pindar and Bucke, Biochem. J. 152:617–622 (1975), specifically incorporated herein by reference, in which formation of mannose-6-phosphate is coupled to NADP reduction by addition of the enzymes phosphomannose isomerase (PMI), phosphoglucose isomerase (PGI), and glucose-6-phosphate dehydrogenase (G6PD).

TABLE 5

Reaction mixture for measurement of phosphomannomutase activity in *Xanthomonas campestris*

| Solution | ml |
|---|---|
| 10 mM NADP | 0.10 |
| 10 mM mannose-1-phosphate | 0.10 |
| 1 mM glucose-1,6-diphosphate | 0.02 |
| coupling enzymes[1] | 0.02 |
| 100 mM cysteine HCl | 0.05 |

TABLE 5-continued

Reaction mixture for measurement of
phosphomannomutase activity in *Xanthomonas campestris*

| Solution | ml |
| --- | --- |
| 100 mM HEPES buffer, pH 7.9 | 0.50 |
| water and extract | 0.21 |

[1]From a mixture of 0.10 ml PMI (380 units/ml), 0.05 ml PGI (2000 units/ml), and 0.05 ml G6PD (1000 units/ml), where one unit will convert 1.0 umole per minute of substrate to product.

Reaction rates became linear after several minutes, the time required for the phosphorylated sugar intermediates to reach steady-state concentrations. These linear rates are proportional to the amount of cytoplasmic extract included in the reaction mixture. For convenience, PMM activity was determined by comparing $NADPH_2$ formation in the presence of mannose-1-phosphate versus that in its absence after a thirty minute incubation, rather than by determining actual reaction rates. Absorbance at 340 nm was measured after thirty minutes' incubation without and with mannose-1-phosphate (M1P). Results are summarized in Table 6.

TABLE 6

Phosphomannomutase activity in cytoplasmic
extracts of sugar nucleotide mutants unable to synthesize
GDP-Mannose. Absorbance at 340 nm was measured after thirty
minutes' incubation without and with mannose-1-phosphate
(M1P).

| Strain | Sugar Nucleotide Defects | MIP-dependent Increase In Abs at 340 nm |
| --- | --- | --- |
| 652 | GDPMan, UDPGlc, UDPGlcA | yes |
| 711 | GDPMan | yes |
| 712 | GDPMan | yes |
| 828 | GDPMan, UDPGlc, UDPGlcA | yes |
| 866 | GDPMan, UDPGlc, UDPGlcA | no |
| 869 | GDPMan | yes |

Initially X866 extracts showed an increase in absorbance at 340 nm after addition of mannose-1-phosphate. However, this increase cannot be attributed to phosphomannomutase activity; the reaction rate was not linear, and a plateau was reached well below the maximum absorbance obtainable. The extract of X866 was still active when assayed for glucose-6-phosphate dehydrogenase activity (0.77 micromoles per ml per minute). Strain X866 clearly is defective in PMM activity.

All other GDP-mannose mutants had phosphomannomutase activity The defective enzyme preventing synthesis of GDP-mannose in these mutuants must be GDP-mannose pyrophosphorylase.

What is claimed is:

1. A method for producing one or more sugar nucleotides comprising:
   (a) culturing a gram-negative microorganism comprising a cloned nucleotide sequence from Xanthomonas encoding at least one enzyme selected from the group consisting of UDP-glucose dehydrogenase, phosphoglucomutase, phosphomannose mutase, GDP-mannose pyrophosphorylase and UDP-glucose pyrophosphorylase under conditions appropriate for the synthesis of at least one sugar nucleotide; and optionally
   (b) harvesting said sugar nucleotide.
2. The method of claim 1, wherein said sugar nucleotide is UDP-glucuronic acid.
3. The method of claim 1, wherein said sugar nucleotide is GDP-mannose.
4. The method of claim 1, wherein said nucleotide sequence is obtained from *Xanthomonas campestris*.
5. The method of claim 1, wherein said gram-negative microorganism is Xanthomonas.
6. The method of claim 1, wherein said gram-negative microorganism is selected from the group consisting of *Pseudomonas putida, Pseudomonas cepacia, Pseudomonas denitrificans, Pseudomonas fluorescens, Pseudomonas stutzeri, Escherichia coli,* and *Enterobacter clocae.*
7. The method of claim 1, wherein said sugar nucleotide is UDP-glucose.
8. A method for producing one or more sugar nucleotides comprising:
   (a) culturing a gram-negative microorganism comprising a vector having a cloned nucleotide sequence from Xanthomonas encoding at least one enzyme selected from the group consisting of UDP-glucose dehydrogenase, phosphoglucomutase, phosphomannose mutase, GDP-mannose pyrophosphorylase and UDP-glucose pyrophosphorylase under conditions appropriate for the synthesis of at least one sugar nucleotide; and optionally
   (b) harvesting said sugar nucleotide,
   wherein said vector containing said nucleotide sequence is selected from the group consisting of pAS7, pAS9 and pTS13.
9. The method of claim 8, wherein said nucleotide sequence is obtained from *Xanthomonas campestris*.
10. The method of claim 8, wherein said gram negative microorganism is Xanthomonas.
11. The method of claim 8, wherein said gram negative microorganism is a selected from a group consisting of *Pseudomonas putida, Pseudomonas cepacia, Pseudomonas denitrificans, Pseudomonas fluorescens, Pseudomonas stutzeri, Escherichia coli,* and *Enterobacter clocae.*
12. The method of claim 8, wherein said sugar nucleotide is UDP-glucuronic acid.
13. The method of claim 8, wherein said sugar nucleotide is GDP-mannose.
14. The method of claim 8, wherein said sugar nucleotide is UDP-glucose.
15. A vector comprising a cloned nucleotide sequence from Xanthomonas encoding at least one enzyme selected from the group consisting of UDP-glucose dehydrogenase, phosphoglucomutase, phosphomannose mutase, GDP-mannose pyrophosphorylase and UDP-glucose pyrophosphorylase.
16. The vector of claim 15, wherein said vector directs microbial synthesis of UDP-glucuronic acid.
17. The vector of claim 15, wherein said vector directs microbial synthesis of GDP-mannose.
18. The vector of claim 15, wherein said nucleotide sequence is obtained from *Xanthomonas campestris*.
19. The vector of claim 15, wherein said vector directs microbial synthesis of UDP-glucose.
20. A gram-negative microorganism comprising the vector of claim 15.
21. The gram-negative microorganism of claim 20, wherein said gram-negative microorganism is Xanthomonas.
22. The gram-negative microorganism of claim 20, wherein said gram-negative microorganism is selected from the group consisting of *Pseudomonas putida, Pseudomonas cepacia, Pseudomonas denitrificans, Pseudomonas fluorescens, Pseudomonas stutzeri, Escherichia coli,* and *Enterobacter clocae.*

23. A vector comprising a nucleotide sequence encoding at least one enzyme selected from the group consisting of UDP-glucose dehydrogenase, phosphoglucomutase, phosphomannose mutase, GDP-mannose pyrophosphorylase and UDP-glucose pyrophosphorylase, wherein said vector is selected from the group consisting of pAS7, pAS9 and pTS13.

24. The vector of claim 23, wherein said vector directs microbial synthesis, of UDP-glucuronic acid.

25. The vector of claim 23, wherein said vector directs microbial synthesis of GDP-mannose.

26. The vector of claim 23, wherein said vector directs microbial synthesis of UDP-glucose.

27. A gram-negative microorganism comprising the vector of claim 23.

28. The gram-negative microorganism of claim 27, wherein said gram-negative microorganism is Xanthomonas.

29. The gram-negative microorganism of claim 27, wherein said gram-negative microorganism is selected from the group consisting of *Pseudomonas putida, Pseudomonas cepacia, Pseudomonas denitrificans, Pseudomonas fluorescens, Pseudomonas stutzeri, Escherichia coli* and *Enterobacter clocae.*

30. A microorganism selected from the group consisting of *X. campestris* X872, *E. coli* LE392 (pAS7), *E. coli* LE392 (pAS9), and *E. coli* LE392 (pTS13).

* * * * *

UNITED STATES PATENT AND TRADEMARK OFFICE
CERTIFICATE OF CORRECTION

PATENT NO. : 5,824,472

DATED : October 20, 1998

INVENTOR(S): MICHAEL R. BETLACH ET AL.

Page 1 of 3

It is certified that error appears in the above-identified patent and that said Letters Patent is hereby corrected as shown below:

COVER PAGE, at [56] OTHER PUBLICATIONS:
"E.S. Creeqer et al." should read --E.S. Creeger et al.--.

COLUMN 1:
Line 26, "poly-saccharides." should read
  --polysaccharides.--

COLUMN 5:
Line 20, "those" should read --1) those--.
Line 34, "inter-mediates" should read --intermediates--.

COLUMN 6:
Line 60, "Theological" should read --rheological--.

COLUMN 10:
Line 41, "glucose-1-phosphate ," should read
  --glucose-1-phosphate,--.

COLUMN 11:
Line 6, "mutants" should read --mutants.--.
Line 20, "wild type" should read --wild-type--.
Line 41, "pTS13" should read --pTS13.--.

COLUMN 13:
Line 51, "This" should read: --¶This--.

UNITED STATES PATENT AND TRADEMARK OFFICE
CERTIFICATE OF CORRECTION

PATENT NO. : 5,824,472

DATED : October 20, 1998

INVENTOR(S) : MICHAEL R. BETLACH ET AL.            Page 2 of 3

It is certified that error appears in the above-identified patent and that said Letters Patent is hereby corrected as shown below:

COLUMN 14:
Line 12, "Strains" should read --¶Strains--.

COLUMN 15:
Line 56, "X1625" should read --X1025--.

COLUMN 16:
Line 40, "mutuants" should read --mutants--.

COLUMN 17:
Line 49, "activity The" should read --activity.  The--.
Line 50, "mutuants" should read --mutants--.

COLUMN 18:
Line 30, "gram negative" should read --gram-negative--.
Line 32, "gram negative" should read --gram-negative--.
Line 33, "a" (first occurrence) should be deleted.

UNITED STATES PATENT AND TRADEMARK OFFICE
CERTIFICATE OF CORRECTION

PATENT NO. : 5,824,472

DATED : October 20, 1998

INVENTOR(S) : MICHAEL R. BETLACH ET AL.

It is certified that error appears in the above-identified patent and that said Letters Patent is hereby corrected as shown below:

COLUMN 19:
Line 9, "synthesis," should read --synthesis--.

Signed and Sealed this

Twenty-seventh Day of July, 1999

Attest:

Q. TODD DICKINSON

*Attesting Officer*     Acting Commissioner of Patents and Trademarks